(12) United States Patent
Imai et al.

(10) Patent No.: US 12,575,737 B2
(45) Date of Patent: *Mar. 17, 2026

(54) ULTRASONIC TRANSMISSION INSTRUMENT AND ULTRASONIC IMAGING DEVICE

(71) Applicant: FUJIFILM CORPORATION, Tokyo (JP)

(72) Inventors: Ryo Imai, Tokyo (JP); Tomohiko Tanaka, Tokyo (JP)

(73) Assignee: FUJIFILM CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/504,471

(22) Filed: Nov. 8, 2023

(65) Prior Publication Data

US 2024/0065556 A1     Feb. 29, 2024

Related U.S. Application Data

(62) Division of application No. 16/860,556, filed on Apr. 28, 2020, now Pat. No. 11,844,587.

(30) Foreign Application Priority Data

May 9, 2019     (JP) ................................ 2019-088916
Aug. 20, 2019     (JP) ................................ 2019-150325

(51) Int. Cl.
   *A61B 5/00*     (2006.01)
   *A61B 8/08*     (2006.01)
   (Continued)

(52) U.S. Cl.
   CPC .......... *A61B 5/0095* (2013.01); *A61B 8/0833* (2013.01); *B06B 1/04* (2013.01);
   (Continued)

(58) Field of Classification Search
   CPC ..... A61B 5/066; A61B 8/0833; A61B 8/0841; A61B 8/4245; A61B 5/0095; G01N 29/2418; G10K 15/046
   See application file for complete search history.

(56) References Cited

U.S. PATENT DOCUMENTS

| | | | |
|---|---|---|---|
| 6,336,899 B1 | 1/2002 | Yamazaki | |
| 2015/0196271 A1* | 7/2015 | Nair ....................... | A61B 8/085 |
| | | | 600/468 |

(Continued)

FOREIGN PATENT DOCUMENTS

| | | |
|---|---|---|
| JP | 5819387 B2 | 10/2015 |
| JP | 2017-506930 A | 3/2017 |
| WO | 2018/221148 A1 | 12/2018 |

OTHER PUBLICATIONS

Mohammadzadeh, M.; Gonzalez-Avila, S.R.; Wan, Y.C.; Wang, X.; Zheng, H.; Ohl,C.D. "Photoacoustic Shock Wave Emission and Cavitation From Structured Optical Fiber Tips" Appl. Phys. Lett. 108, 024101 (2016).

(Continued)

*Primary Examiner* — Amelie R Davis
(74) *Attorney, Agent, or Firm* — Volpe Koenig

(57)     ABSTRACT

To provide an ultrasonic transmission instrument that can uniformly transmit ultrasonic waves in each direction around the instrument, even when the instrument is made of a material through which the ultrasonic waves cannot be transmitted. In an ultrasonic transmission instrument according to the invention, a light transmission member is disposed at an emission end of an optical waveguide, and an outer peripheral member covers an outer periphery of the light transmission member and is made of a light absorbing material.

14 Claims, 14 Drawing Sheets

(51) Int. Cl.

| | |
|---|---|
| B06B 1/04 | (2006.01) |
| G01N 29/24 | (2006.01) |
| G02B 6/10 | (2006.01) |
| G10K 11/28 | (2006.01) |

(52) U.S. Cl.

CPC .......... G10K 11/28 (2013.01); B06B 2201/76 (2013.01); G01N 29/2418 (2013.01); G02B 6/10 (2013.01)

(56) References Cited

U.S. PATENT DOCUMENTS

| | | |
|---|---|---|
| 2015/0297092 A1 | 10/2015 | Irisawa |
| 2016/0213256 A1 | 7/2016 | Li et al. |
| 2019/0216425 A1* | 7/2019 | Yamamoto ............... A61B 8/06 |
| 2020/0093372 A1 | 3/2020 | Irisawa |

OTHER PUBLICATIONS

Lan, Lu; Xia, Yan; Li, Rui; Liu, Kaiming; Mai, Jieying; Medley, Jennifer Anne; OBENG-GYASI, Samilia; Han, Linda K., A Fiber Optoacoustic Guide With Augmented Reality for Precision Breast-Conserving Surgery, Light: Science & Applications (2018) 7:2.

Japanese Office Action issued on Jan. 24, 2023 for Japanese Patent Application No. 2019-150325.

* cited by examiner

DIRECTION OF ULTRASONIC PROBE

TREATMENT AND
EXAMINATION INSTRUMENT

LIGHT
ABSORBER

OPTICAL FIBER

FIG. 3
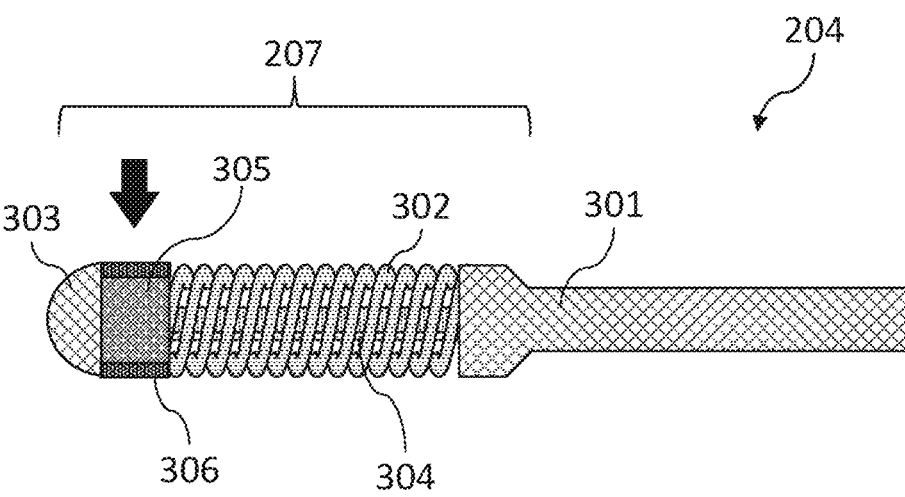
CROSS-SECTIONAL VIEW OF
PORTION INDICATED BY ARROW
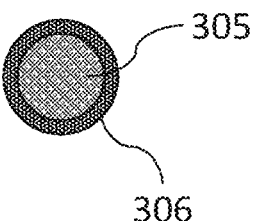

FIG. 4
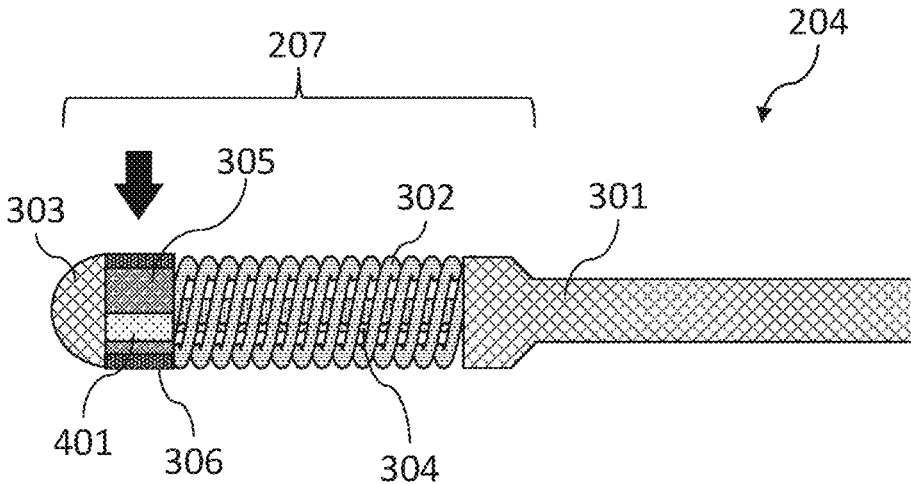
CROSS-SECTIONAL VIEW OF
PORTION INDICATED BY ARROW
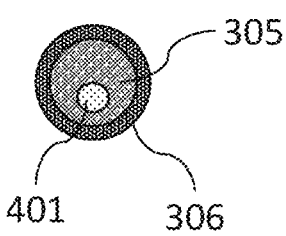
FIG. 5
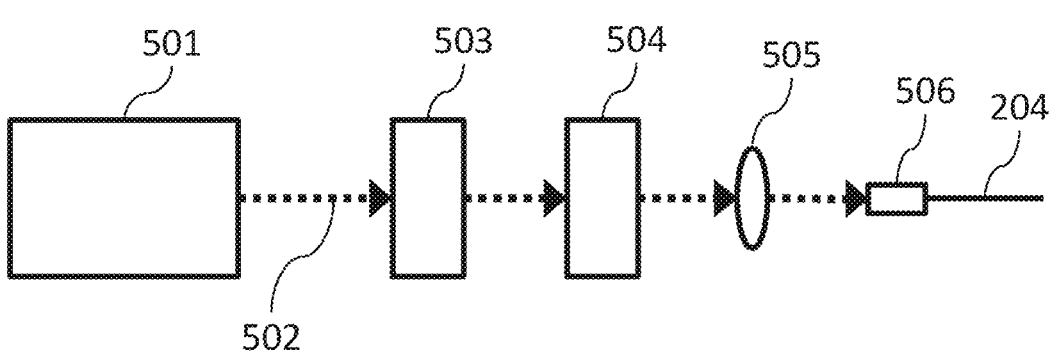

FIG. 7

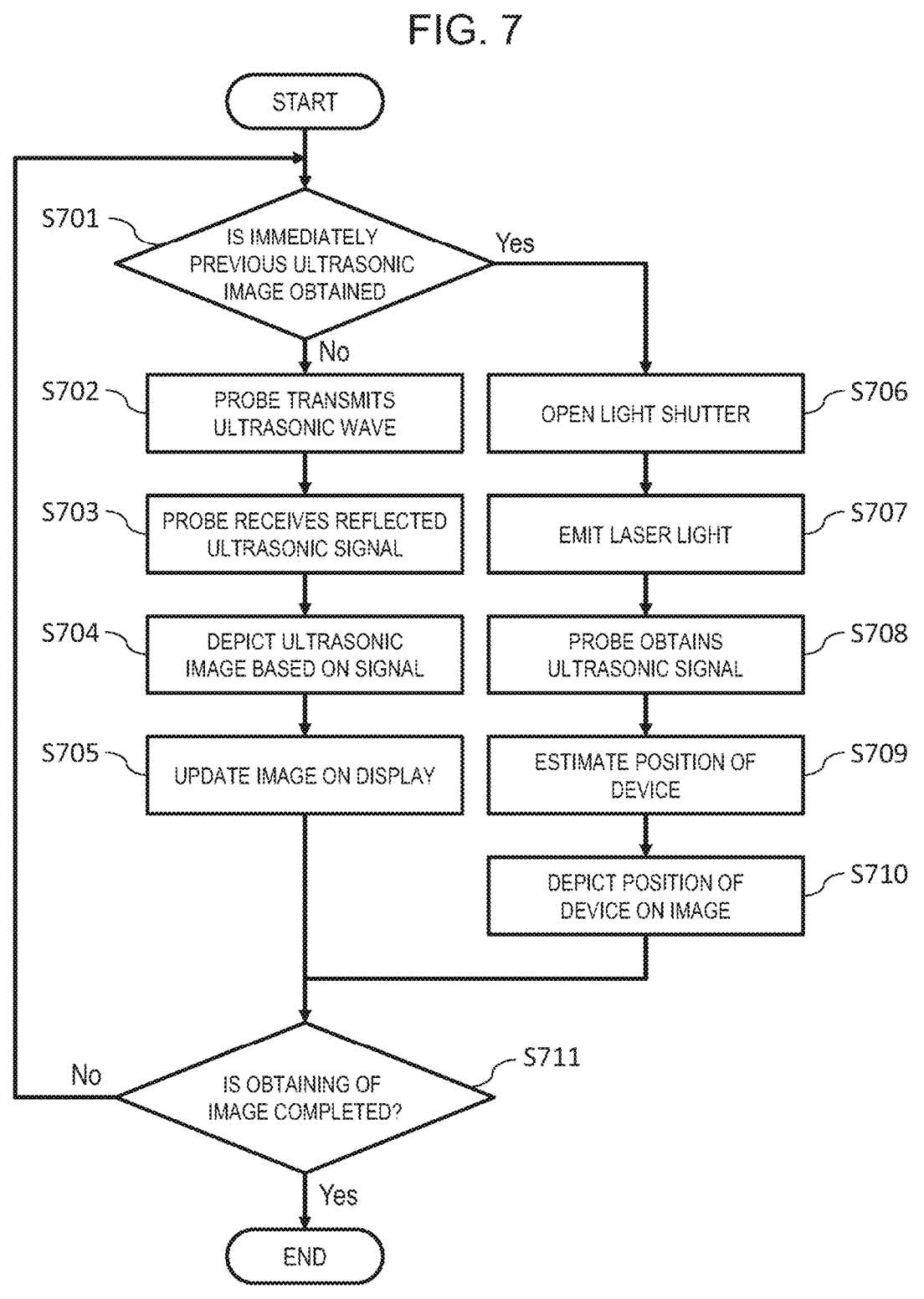

```
                        ┌─────────┐
                        │  START  │
                        └────┬────┘
                             │
                             ▼
S701 ───◇─────────────────────────────◇
        │  IS IMMEDIATELY               │  Yes
        │  PREVIOUS ULTRASONIC          ├──────────┐
        │  IMAGE OBTAINED               │          │
        ◇─────────────┬─────────────────◇          │
                      │ No                          │
                      ▼                             ▼
S702 ──┌──────────────────────┐    ┌──────────────────────┐── S706
       │  PROBE TRANSMITS      │    │  OPEN LIGHT SHUTTER   │
       │  ULTRASONIC WAVE      │    │                       │
       └──────────┬───────────┘    └──────────┬────────────┘
                  ▼                            ▼
S703 ──┌──────────────────────┐    ┌──────────────────────┐── S707
       │ PROBE RECEIVES REFLECTED│  │  EMIT LASER LIGHT     │
       │  ULTRASONIC SIGNAL     │   │                       │
       └──────────┬───────────┘    └──────────┬────────────┘
                  ▼                            ▼
S704 ──┌──────────────────────┐    ┌──────────────────────┐── S708
       │  DEPICT ULTRASONIC    │    │  PROBE OBTAINS        │
       │  IMAGE BASED ON SIGNAL │   │  ULTRASONIC SIGNAL    │
       └──────────┬───────────┘    └──────────┬────────────┘
                  ▼                            ▼
S705 ──┌──────────────────────┐    ┌──────────────────────┐── S709
       │ UPDATE IMAGE ON DISPLAY│   │  ESTIMATE POSITION OF │
       │                       │    │  DEVICE               │
       └──────────┬───────────┘    └──────────┬────────────┘
                  │                            ▼
                  │               ┌──────────────────────┐── S710
                  │               │  DEPICT POSITION OF   │
                  │               │  DEVICE ON IMAGE      │
                  │               └──────────┬────────────┘
                  │                          │
                  ▼                          │
           ◇────────────────────◇◄──────────┘── S711
    No     │  IS OBTAINING OF    │
  ┌────────│  IMAGE COMPLETED?   │
  │        ◇─────────┬──────────◇
  │                  │ Yes
  │                  ▼
  │             ┌─────────┐
  │             │   END   │
  │             └─────────┘
  └── (back to START)
```

START

S701 — IS IMMEDIATELY PREVIOUS ULTRASONIC IMAGE OBTAINED — Yes / No

S702 — PROBE TRANSMITS ULTRASONIC WAVE

S703 — PROBE RECEIVES REFLECTED ULTRASONIC SIGNAL

S704 — DEPICT ULTRASONIC IMAGE BASED ON SIGNAL

S705 — UPDATE IMAGE ON DISPLAY

S706 — OPEN LIGHT SHUTTER

S707 — EMIT LASER LIGHT

S708 — PROBE OBTAINS ULTRASONIC SIGNAL

S709 — ESTIMATE POSITION OF DEVICE

S710 — DEPICT POSITION OF DEVICE ON IMAGE

S711 — IS OBTAINING OF IMAGE COMPLETED? — No / Yes

END

FIG. 9
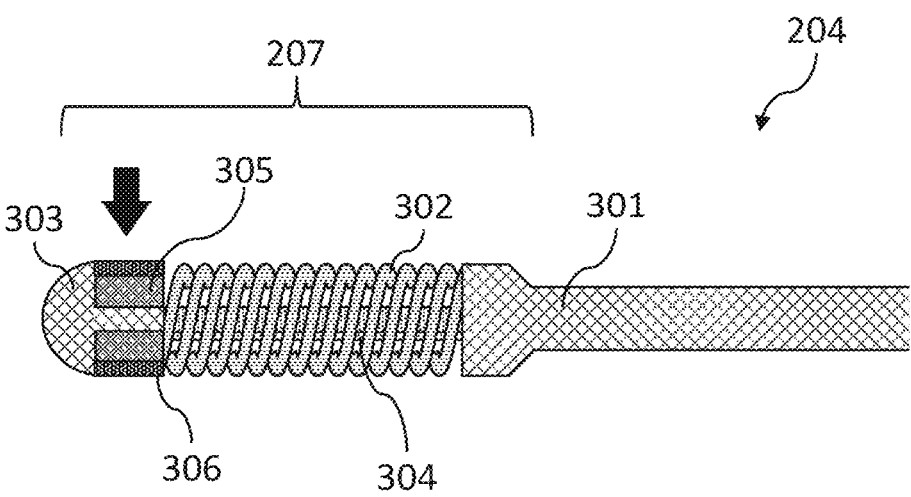
CROSS-SECTIONAL VIEW OF
PORTION INDICATED BY ARROW
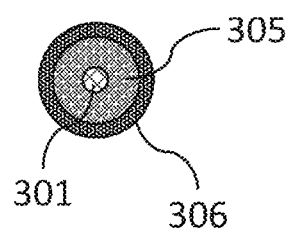
FIG. 10
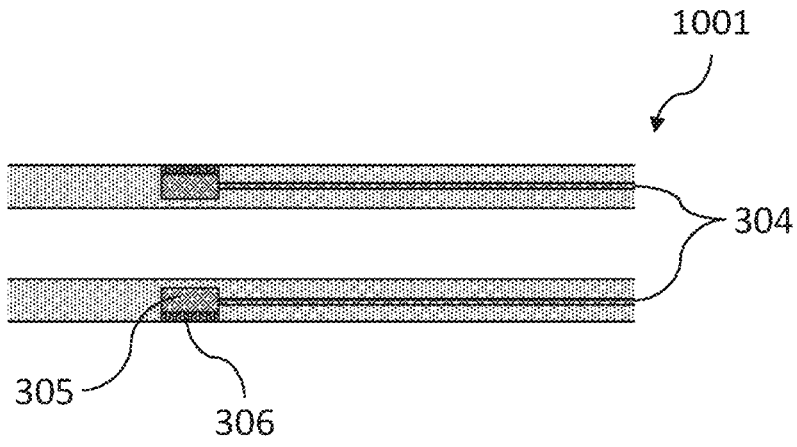

-Prior Art --

-Prior Art--

ULTRASONIC TRANSMISSION INSTRUMENT AND ULTRASONIC IMAGING DEVICE

CROSS-REFERENCE TO RELATED APPLICATION

This application is a divisional of U.S. patent application Ser. No. 16/860,556, filed Apr. 28, 2020, which claims priority to Japanese Patent Application No. 2019-088916, filed May 9, 2019, and Japanese Patent Application No. 2019-150325, filed Aug. 20, 2019, each of which is incorporated herein by reference in its entirety.

BACKGROUND OF THE INVENTION

1. Field of the Invention

The present invention relates to an ultrasonic transmission instrument that transmits an ultrasonic wave, and an ultrasonic imaging device that images an ultrasonic image.

2. Description of the Related Art

There are treatment methods for performing treatment in a body in a minimally invasive manner using a small-diameter treatment instrument such as a catheter. In such treatment, the treatment instrument is inserted into the body after a needle or the like is pierced through a body surface, so that burden on a patient is smaller than that in laparotomy and thoracotomy surgery, but it is necessary to obtain an image of a treatment site with a device for imaging inside of the body because the treatment instrument cannot be seen directly. As an example of such minimally invasive treatment, there is a method of treating stenosis and occlusion sites of a blood vessel with an instrument such as a catheter. In order to specify a position of the instrument during treatment, an X-ray imaging device capable of obtaining fluoroscopic images of the living body in a wide range is widely used. On the other hand, there is a problem that in X-ray imaging, body tissue other than bones are hardly reflected, so that it is necessary to use a contrast agent in combination, but only an area where blood flow exists can be imaged with the contrast agent, the occlusion site cannot be imaged. Therefore, ultrasonic imaging is sometimes used as a supplement. The ultrasonic imaging can depict blood vessels or the like without the need for the contrast agent, and does not need to expose the blood vessels.

In the examination and treatment using the ultrasonic guide as described above, an affected part or a vicinity of the small-diameter medical instrument is depicted, and the examination and treatment instrument is advanced based on the image. In the treatment using the catheter or the like, a blood vessel in a vicinity of a stenosis and occlusion site is depicted, and the instrument is advanced so as not to get out of the blood vessel. However, in the examination and treatment using the ultrasonic guide, there are problems that the instrument may get out of an ultrasonic imaging area, and it is sometimes difficult to distinguish a tip end portion of the catheter or the like on an image.

As a method that can solve the above-described problem, a technique has been devised in which an ultrasonic wave is generated from an instrument and a position of the instrument is determined by using the ultrasonic wave as a position detection signal (PTL 1: Japanese Patent No. 5819387). In this technique, obtaining of an ultrasonic image and obtaining of a signal from an ultrasonic generation source is alternately repeated to depict the position of the instrument on the ultrasonic image. In such a technique, it is necessary to dispose an ultrasonic generation source in a small-diameter instrument, for example, having a diameter of 1 mm or less. Therefore, a technique of generating an ultrasonic wave by using an optical fiber having a diameter of several hundred μm or less and a light absorbing material attached to a tip end portion of the optical fiber based on a photo-acoustic effect is promising as an ultrasonic generation source. The photo-acoustic effect is an effect in which a short pulse laser is emitted to a light absorbing material to cause a local rapid temperature rise, and an ultrasonic wave is generated by thermal expansion caused by the temperature rise. PTL 1 also uses the photo-acoustic effect for generating an ultrasonic wave.

In the case of using the technique of generating an ultrasonic wave by using the photo-acoustic effect, it is necessary to dispose an optical fiber and a light absorber for generating a photo-acoustic signal in an instrument such as a catheter. However, a propagation state of the generated ultrasonic signal changes depending on members and structures of the instrument. In particular, in a case where the instrument is made of a material such as metal whose acoustic impedance is significantly different from that of surrounding living tissue, there are problems that (a) the generated ultrasonic wave does not propagate in a specific direction, and (b) when the ultrasonic generation source is provided inside the instrument, the ultrasonic wave is blocked by a metal member, and is significantly attenuated when the ultrasonic wave gets out of the instrument.

PTL 1 describes an example in which an ultrasonic generation mechanism is provided inside a needle of a puncture needle. Since the puncture needle is used with a hole inside the needle directed toward a body surface side, the ultrasonic signal is not hidden by the metal needle. However, an axially symmetric device such as a catheter is not limited to the above, and the above-described problems may occur. PTL 1 does not disclose a solution to those problems.

SUMMARY OF THE INVENTION

The invention has been made in view of the above-described problems, and an object of the invention is to provide an ultrasonic transmission instrument that can uniformly transmit ultrasonic waves in each direction around the instrument, even when the instrument is made of a material through which the ultrasonic waves cannot be transmitted.

An ultrasonic transmission instrument according to the invention is configured such that a light transmission member is disposed at an emission end of an optical waveguide, and an outer peripheral member covers an outer periphery of the light transmission member and is made of a light absorbing material.

An ultrasonic transmission instrument according to the invention can uniformly generate ultrasonic waves in each direction around the instrument, even when the instrument is made of a material such as metal through which the ultrasonic waves cannot be transmitted.

BRIEF DESCRIPTION OF THE DRAWINGS

FIG. 3 is a structural diagram of a guide wire 204 according to Embodiment 1.

FIG. 4 shows a configuration example in which a light scattering member 401 is disposed in a window portion 305.

FIG. 5 shows a mechanism for introducing a laser light into the guide wire 204.

FIG. 7 is a flowchart showing an operation sequence of the position detection system 200.

FIG. 9 is a structural diagram of the guide wire 204 according to Embodiment 2.

FIG. 10 shows an example in which the window portion 305 is formed in a cylindrical shape.

DESCRIPTION OF THE PREFERRED EMBODIMENTS

<Problems in Ultrasonic Transmission Instrument in Related Art>

Figure 1:
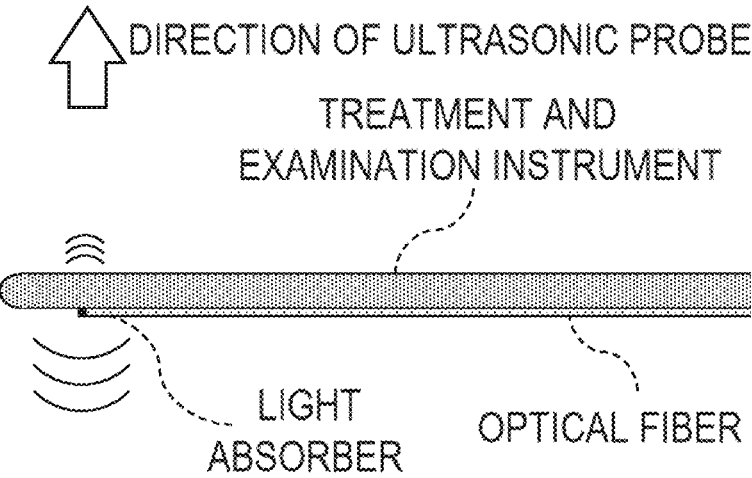
FIG. 1 is a diagram showing a configuration example of an ultrasonic transmission instrument in the related art.

FIG. 1 is a diagram showing a configuration example of an ultrasonic transmission instrument in the related art. It is assumed that FIG. 1 shows an example in which an ultrasonic generation source is attached beside an elongated treatment and examination instrument such as a catheter. An optical fiber extends parallel to the instrument, and a light absorber is attached to a tip end of the optical fiber. The light absorber acts as an ultrasonic transmission source due to a photo-acoustic effect when light is emitted to the light absorber.

In treatment under an ultrasonic imaging guide, a small-diameter instrument such as a catheter is often imaged from a side of the instrument. However, since the instrument such as a catheter can rotate around an axis thereof, when the instrument is oriented in a direction in which an ultrasonic wave is difficult to propagate, a position of the instrument may not be specified. Specifically, as shown in FIG. 1, when the ultrasonic generation source is located on an opposite side of an ultrasonic probe (ultrasonic transceiver) so as to sandwich the treatment and examination instrument, an intensity of an ultrasonic wave generated in a direction of the ultrasonic probe is weakened due to blocking of the instrument. In particular, a problem is more serious when the instrument, such as a guide wire used in catheter treatment, is made of a material, such as metal, whose acoustic impedance is significantly different from that of a living body.

Embodiment 1

Figure 2:
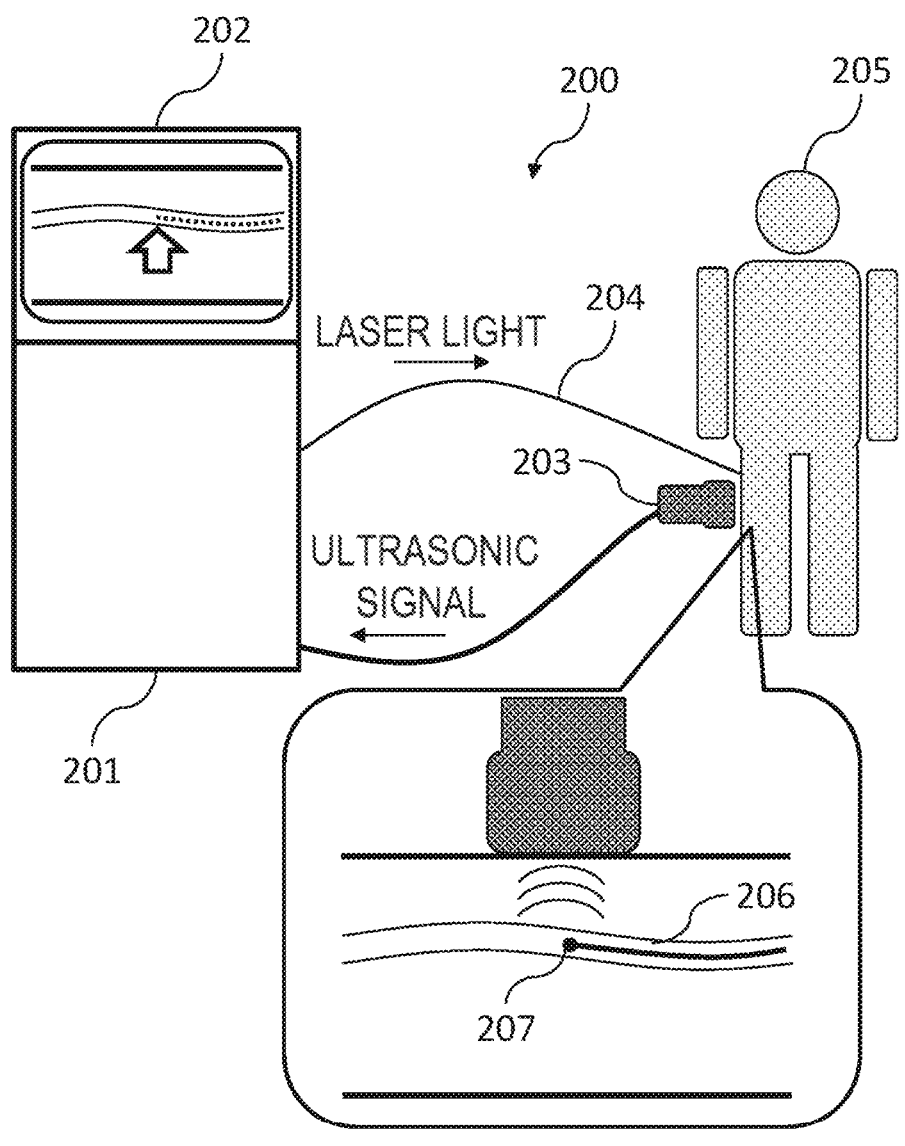
FIG. 2 is a configuration diagram of a position detection system 200 according to Embodiment 1.

FIG. 2 is a configuration diagram of a position detection system 200 according to Embodiment 1 of the invention. Here, as an example of the position detection system 200, a configuration example for detecting a tip end position of a guide wire (small-diameter instrument) used in the catheter treatment will be described. However, it should be noted that an application of the invention is not limited to the guide wire, but can be applied to a small-diameter medical instrument having similar shapes and uses.

The position detection system 200 includes an ultrasonic imaging device 201 in which a pulse laser is mounted, a display 202 for displaying an image, an ultrasonic probe 203 for transmitting and receiving an ultrasonic wave, and a guide wire 204 on which an ultrasonic transmission instrument 207 is mounted. In treatment of a blood vessel using a catheter, the guide wire 204 is inserted into a blood vessel 206 of a subject 205. By imaging a tomographic image in a vicinity of the blood vessel by the ultrasonic imaging device 201 and the ultrasonic probe 203, an operator can grasp a structure of a treatment target. In the position detection system using an ultrasonic beacon, the ultrasonic transmission instrument 207 is attached to a tip end portion of the guide wire 204, the ultrasonic probe 203 receives a generated ultrasonic wave to estimate a tip end position, and the tip end position is superimposed in an ultrasonic image shown on the display 202. Accordingly, even when the guide wire 204 is not visible on the image, a position of the tip end portion can be easily grasped. Further, since the position of the tip end portion can be determined even outside a depiction area of the ultrasonic image, even when the ultrasonic transmission instrument 207 is outside the depiction area, a direction in which the ultrasonic transmission instrument 207 exists can be indicated.

The guide wire 204 used for vascular treatment has thickness of 0.5 mm or less. Therefore, an ultrasonic generation mechanism also needs to be this size or smaller. A piezo element is generally used as the ultrasonic generation mechanism, but it is difficult to dispose and wire a piezo element having a size of 0.5 mm or less in the guide wire 204. On the other hand, an ultrasonic generation mechanism using the photo-acoustic effect is suitable for being incorporated in such a small-diameter instrument. The photo-acoustic effect is a phenomenon in which a pulsed ultrasonic wave is generated when a light absorbing material is irradiated with pulse laser light. When an object that absorbs light is irradiated with the pulse laser light, a temperature of the object is rapidly raised locally due to absorption of the pulse laser light. A volume of the object expands locally due to the rapid temperature rise, and an ultrasonic wave is generated by the expansion. It is known that such an ultrasonic wave is generated efficiently when a pulse width of the pulse laser light is on the order of nanoseconds.

A diameter of the optical fiber is about several hundred μm even when a protective coating is included, and the diameter is 200 μm or less if the optical fiber is thin. Therefore, the optical fiber can be embedded in the guide wire 204 having the diameter of 0.5 mm or less. By disposing the light absorber on the tip end of the optical fiber and introducing the pulse laser light from an end of the optical fiber, an ultrasonic wave can be generated in the tip end portion.

As shown in FIG. 2, the position detection system 200 detects the ultrasonic wave generated toward a side surface of the guide wire 204 by using the ultrasonic probe 203. However, since a direction of the guide wire 204 is not constant and the guide wire 204 can rotate around an axis, it is necessary to generate ultrasonic waves toward all directions around the guide wire 204 in order to keep track of a signal from the guide wire 204. However, since the guide wire 204 is made of a metal material that strongly reflects ultrasonic waves, a shadow of the guide wire 204 is formed by simply attaching the optical fiber to the side surface of the guide wire 204, and the ultrasonic waves are difficult to propagate in a direction opposite to the optical fiber. On the other hand, when a part of the guide wire 204 is to be made of an ultrasonic-permeable member, it is necessary to use an ultrasonic-permeable soft material, but strength of the guide wire 204 may not be maintained.

FIG. 3 is a structural diagram of an inside of the guide wire 204 according to Embodiment 1. The guide wire 204 includes a wire portion 301 made of metal or alloy constituting a guide wire body, a coil portion 302, a tip end portion 303 (opaque member), an optical fiber 304 (optical waveguide) for generating an ultrasonic signal, a window portion 305 (light transmission member) through which a light can be transmitted, and a light absorber 306 applied around the window portion. The pulse laser light for generating an ultrasonic wave is introduced into the window portion 305 through the optical fiber 304. The pulse laser light is diffused in the window portion 305 and is absorbed when the pulse laser light hits the light absorber 306 to generate the ultrasonic wave. It is desirable that the window portion 305 and the light absorber 306 are provided over the entire periphery in order to generate ultrasonic waves in all directions of the guide wire 204. However, for example, even when the light absorber 306 is disposed so as to cover only a part of an outer periphery of the window portion 305, an ultrasonic wave can be generated from the covered portion, so that to this extent, the effect of Embodiment 1 can be exhibited.

FIG. 4 shows a configuration example in which a light scattering member 401 is disposed in the window portion 305. Since light emitted from the optical fiber 304 normally propagates in a forward direction, the light does not diffuse uniformly in the window portion 305. When non-uniformity of such laser light is a problem, the light scattering member 401 is disposed in front of the optical fiber 304 to scatter the light, so that the laser light can diffuse uniformly in the window portion 305. In this example, a hole is formed in a part of the transparent window portion 305, and the light scattering member 401 is provided in this hole. The light scattering member 401 can be made of a transparent resin or the like mixed with fine particles of plastic or the like that does not absorb the laser light to be used. In a case where a sufficient strength can be ensured by the light scattering member 401, all the window portions 305 may be replaced with the light scattering member 401.

FIG. 5 shows a mechanism for introducing laser light into the guide wire 204. First, laser light 502 is emitted from a laser 501 that generates a photo-acoustic signal. In order to generate the photo-acoustic signal, the laser needs to be a pulse laser having a pulse width on the order of nanoseconds. Immediately behind the laser, a shutter 503 for switching ON/OFF of the laser light is provided. Thereafter, the laser light is adjusted to an appropriate power by an attenuator 504. The laser light whose power has been adjusted is condensed by a lens 505 and introduced into the optical fiber 304 in the guide wire 204 to which a connector 506 of the optical fiber is attached. The guide wire 204 is used to attach another treatment instrument from a distal end portion. Therefore, it is required that the connector 506 can be easily removed or cut so as not to hinder an insertion of another instrument. As described above, the laser 501 needs to be a laser having a pulse width on the order of nanoseconds, but an oscillation wavelength of an most common and inexpensive Nd:YAG laser is invisible with infrared light. In order to make it possible to visually determine light leakage, a visible light laser that is coaxial with the pulse laser for generating the photo-acoustic signal and has a power that does not impair eyes of the operator may be introduced.

Figure 6:
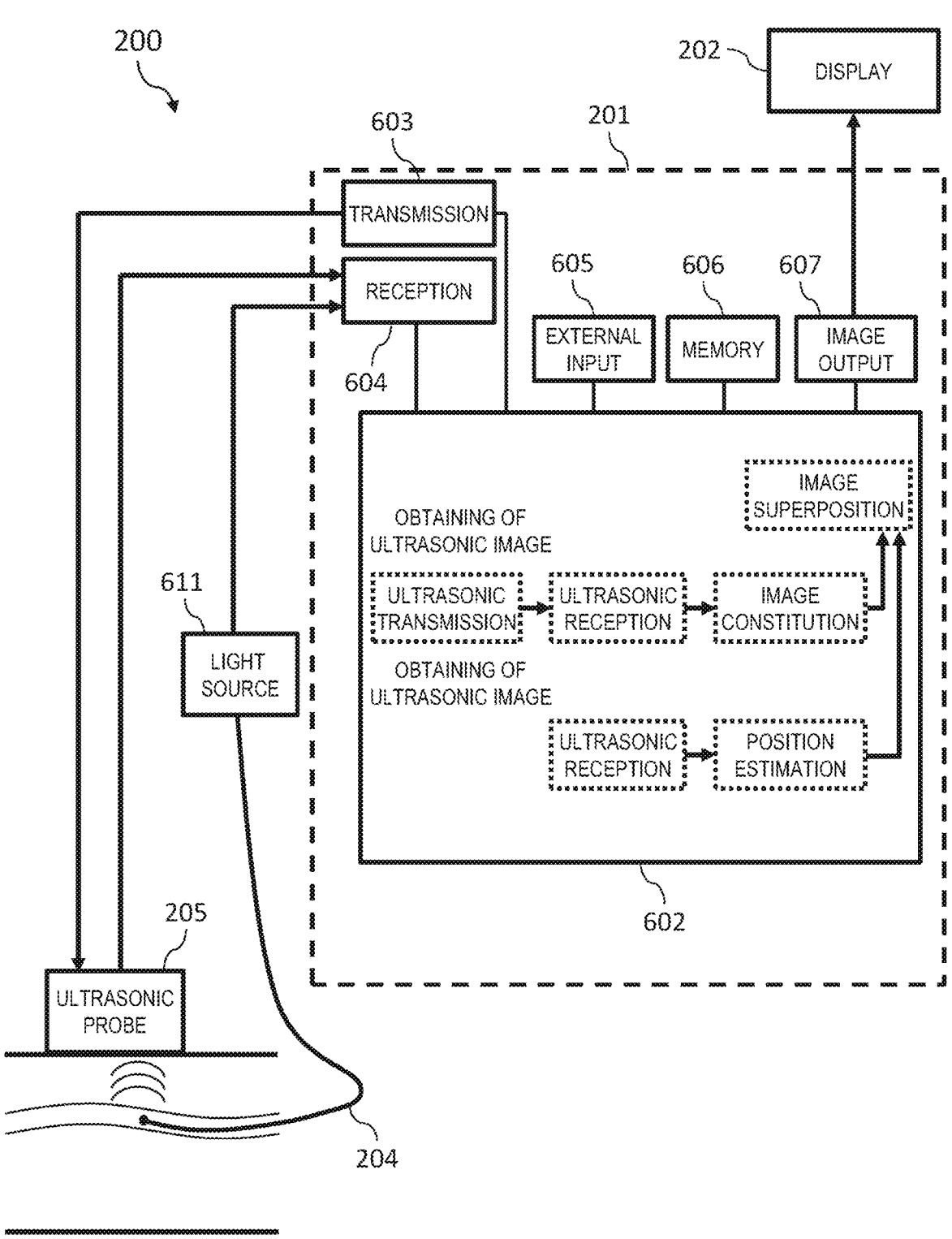
FIG. 6 is a detailed configuration diagram of the position detection system 200.

FIG. 6 is a detailed configuration diagram of the position detection system 200. The ultrasonic imaging device 201 includes a calculation unit 602, a transmission unit 603 for transmitting an ultrasonic wave and a reception unit 604 for receiving an ultrasonic wave, an external input 605, a memory 606, an image output unit 607, and the display 202. The ultrasonic probe 203 includes an ultrasonic probe therein, generates an ultrasonic wave by a power from the transmission unit 603, and transmits the received ultrasonic signal to the reception unit 604. The guide wire 204 is connected to a laser light source 611, and an ultrasonic wave is generated at the tip end of the guide wire 204 by pulse laser light output from the laser light source 611. The laser light source 611 having a pulse width on the order of nanoseconds generates pulse laser light at a unique frequency, and transmits a pulse generation timing signal to the reception unit 604. Obtaining of an ultrasonic image and estimation of an instrument position is alternately performed under control of the calculation unit 602, and an image on which both are superimposed is displayed on the display 202.

FIG. 7 is a flowchart showing an operation sequence of the position detection system 200. In the position detection system 200, the obtaining of the ultrasonic image and position obtaining using an ultrasonic signal from the ultrasonic transmission instrument 207 is alternately performed, and images obtained as a result are superimposed, and thus the position of the ultrasonic transmission instrument 207 is depicted on the image. Hereinafter, each step of FIG. 7 will be described.

(FIG. 7: Step S701)

The calculation unit 602 determines whether to perform the obtaining of the ultrasonic image or the estimation of the instrument position. Here, as an example, the obtaining of the ultrasonic image and the estimation of the instrument position is alternately performed. The obtaining of the ultrasonic image and the estimation of the instrument position do not necessarily have to be performed alternately, and it is sufficient that an update is performed between both processes to such an extent that a large displacement does not occur between both processes. When the obtaining of the ultrasonic image is performed, the same step as in a general ultrasonic imaging system is performed. FIG. 7 shows simplified steps.

(FIG. 7: Steps S702 to S705)

When the ultrasonic image is obtained, S702 to S705 are performed. The ultrasonic probe 203 transmits an ultrasonic wave (S702). The ultrasonic probe 203 receives an ultrasonic signal reflected from the subject 205 (S703). The calculation unit 602 constitutes an image based on the ultrasonic signal received in S703 (S704), and displays the image on the display (S705).

(FIG. 7: Steps S706 to S710)

When the position of the ultrasonic transmission instrument 207 is estimated, S706 to S710 are performed. First, the shutter 503 that blocks laser light is opened (S706), and the laser light is emitted to the light absorber 306 in a vicinity of the tip end of the guide wire 204 (S707). An ultrasonic wave is generated when the light absorber 306 is irradiated with the laser light, and the ultrasonic wave is received by the ultrasonic probe 203 (S708). The calculation unit 602 estimates the position of the ultrasonic transmission instrument 207 based on a waveform of the received ultrasonic wave (S709), superimposes the position on the ultrasonic image, and depicts the position on the display 202 (S710).

The calculation unit 602 can use, for example, the following method as a method of estimating the position of the ultrasonic transmission instrument 207. As an example, a part of the pulse laser light is received by a photodetector, and this signal is used as a trigger to obtain an ultrasonic waveform. Usually, a plurality of ultrasonic reception elements are provided in the ultrasonic probe 203, and the position of the ultrasonic transmission instrument 207 can be estimated from a difference between reception time points of ultrasonic signals observed by the respective reception elements.

Figure 8:
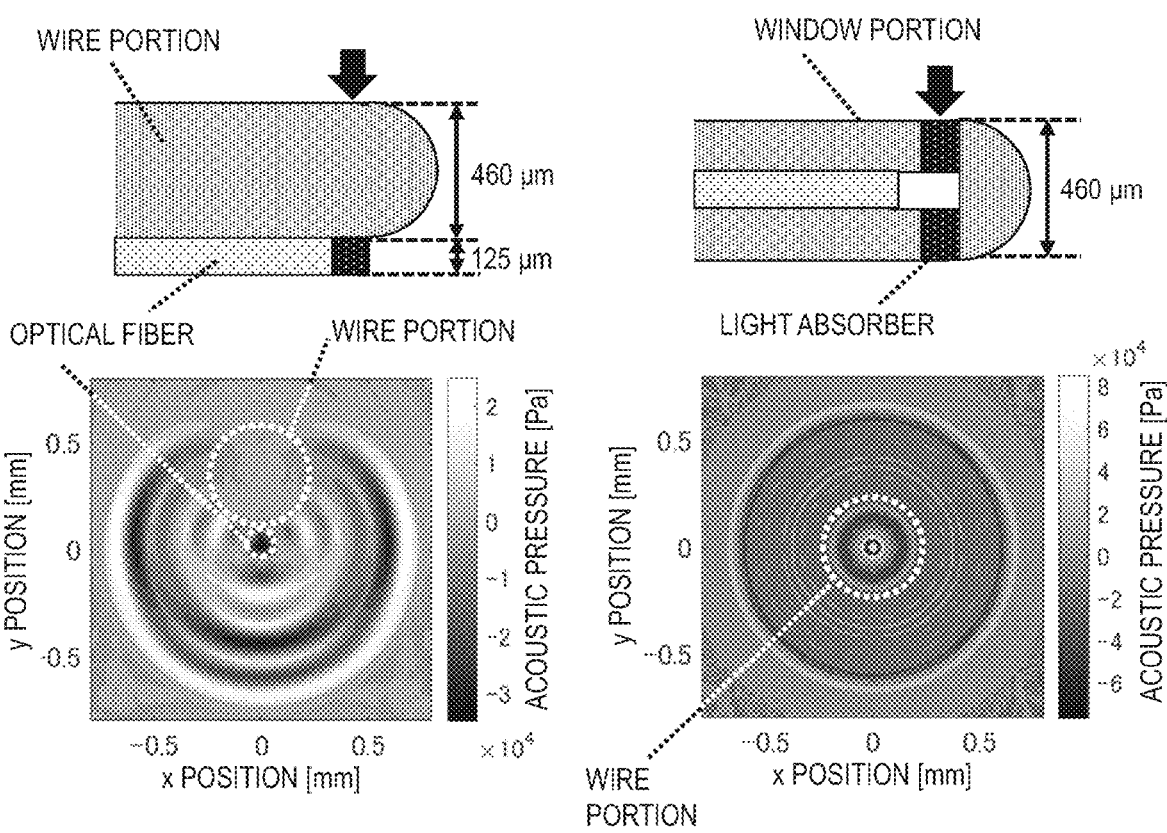
FIG. 8 is a diagram showing an effect of Embodiment 1 by simulation.

FIG. 8 shows a diagram showing the effect of the invention by simulation. FIG. 8 is a diagram simulating a propagation state of the ultrasonic wave generated by the photoacoustic effect regarding a case where the ultrasonic generation mechanism is attached to a side surface of the wire portion as shown in FIG. 1 and a structure of the invention shown in FIG. 3. In the simulation, a structure shown in an upper portion of FIG. 8 is used. The wire portion is assumed to be iron, and a light absorbing member is assumed to be colored silicon rubber. In this structure, the pulse laser light is emitted through the optical fiber, and the propagation of the ultrasonic wave generated by the photoacoustic effect is calculated three-dimensionally and periodically.

Acoustic pressure distributions in cross-sections at positions shown by arrows in structural diagrams on an upper portion of FIG. 8 are shown on a lower portion of FIG. 8. The lower portion of FIG. 8 shows pressure distributions at 0.45 μs after irradiation of the laser light. It can be seen that, in a structure on a left side of FIG. 8 where the light absorber is provided on the side surface of the wire portion, the generated ultrasonic waves are blocked by the wire portion and the ultrasonic waves do not propagate in an upward direction where the wire portion exists. On the other hand, it can be seen that, in a structure of the invention on a right side of FIG. 8, the ultrasonic waves propagate isotropically.

Embodiment 1: Overview

In the ultrasonic transmission instrument 207 according to Embodiment 1, the window portion 305 through which light is transmitted is disposed in the small-diameter instrument (guide wire 204) such as a catheter, and the light absorber 306 for generating the photo-acoustic signal is disposed on an outer peripheral portion of the window portion 305. The window portion 305 can have an axially symmetric structure or a structure similar thereto, such as a cylindrical shape, so as to uniformly generate ultrasonic waves in directions around an axis of the ultrasonic transmission instrument 207. Accordingly, the ultrasonic waves can be uniformly generated in each direction around the tip end portion without being blocked by a metal portion of the guide wire 204 body.

Embodiment 2

In Embodiment 2 of the invention, a structure of a small-diameter instrument different from Embodiment 1 will be described. In order to specifically describe a form of the invention as in Embodiment 1, a small-diameter instrument used in catheter treatment will be described as an example. An overall configuration and operation steps of the position detection system 200 are similar to those in Embodiment 1, and a description thereof will be omitted.

FIG. 9 is a structural diagram of an inside of the guide wire 204 according to Embodiment 2. It is similar to Embodiment 1 in that the wire portion 301, the coil portion 302, and the tip end portion 303 are provided. A difference from Embodiment 1 is that the window portion 305 is disposed around the tip end portion of the wire portion 301. With such a structure, a requirement for a mechanical strength of the window portion 305 can be reduced as compared with Embodiment 1. As in Embodiment 1, the window portion 305 and the light absorber 306 are desirably provided over the entire periphery in order to generate ultrasonic waves for position detection in all directions.

Since there is an opaque material (wire portion 301) at a center of the window portion 305, a uniformity of diffusion of the laser light emitted from the optical fiber 304 is reduced, and a distribution of an intensity of the generated ultrasonic waves is non-uniform in a circumferential direction of the wire. In a case where the non-uniformity of the diffusion of the laser light is a problem, by providing the light scattering member in front of the optical fiber 304 as in Embodiment 1, the laser light can diffuse uniformly in the window portion 305. As in Embodiment 1, the light scattering member can be made of a transparent resin or the like mixed with fine particles of plastic or the like that does not absorb the laser light to be used.

FIG. 10 is an example in which the window portion 305 is formed in a cylindrical shape. The configuration according to the invention can be used even when a small-diameter instrument 1001 such as a catheter has a cylindrical shape through which a wire or another instrument passes in the center. In this case, the window portion 305 formed in the cylindrical shape can be disposed inside the small-diameter instrument 1001 and on an outer periphery of a hollow portion of the small-diameter instrument 1001. The light absorber 306 is disposed on the outer periphery of the window portion 305 as in Embodiment 1. In general, a diameter of the small-diameter instrument 1001 that allows an instrument to pass through the inside thereof is allowed to be larger than that of the guide wire 204 described in Embodiment 1. If there is room in a diameter size, by mounting a plurality of optical fibers in the small-diameter instrument 1001, uniformity of diffusion of light can be improved, and ultrasonic waves can be generated more isotropically.

Embodiment 3

In Embodiment 3 of the invention, a structure of a small-diameter instrument different from Embodiments 1 and 2 will be described. In order to specifically describe a form of the invention as in Embodiment 1, a small-diameter instrument used in catheter treatment will be described as an example. The overall configuration and the operation steps of the position detection system 200 are similar to those in Embodiment 1, and the description thereof will be omitted.

Figure 11:
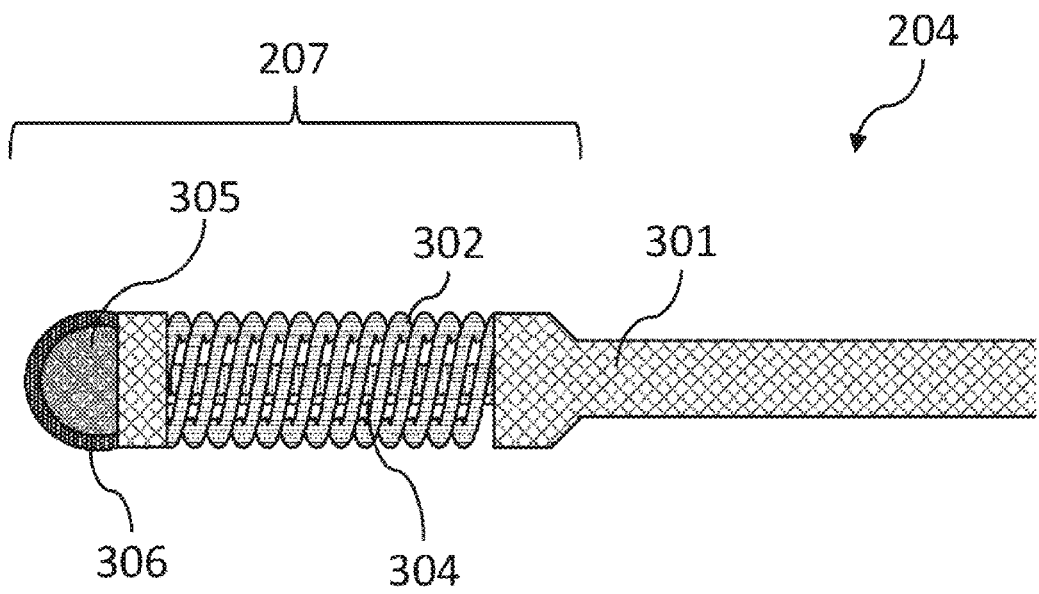
FIG. 11 is a structural diagram of the guide wire 204 according to Embodiment 3.

FIG. 11 is a structural diagram of an inside of the guide wire 204 according to Embodiment 3. It is similar to Embodiment 1 in that the wire portion 301 and the coil portion 302 are provided. A difference from Embodiment 1 is that the window portion 305 also serves as the tip end portion 303 and is provided at the tip end portion of the guide wire 204. When a non-scattering material such as a quartz glass sphere is provided as the window portion 305, light emitted from the optical fiber 304 is emitted in a forward direction of the instrument, and a strong ultrasonic wave is generated in the forward direction. When a resin mixed with a scatterer is used as the window portion 305, the light is scattered in the window portion 305, and uniform ultrasonic waves are generated in all directions. In a case where the window portion 305 is provided at the tip end portion, the window portion 305 directly hits living tissue, so that mechanical durability is required. On the other hand, a position of a signal generation source is the same as that of the tip end of the guide wire 204, and errors in estimating the position of the tip end of the instrument, which is important for grasping during treatment, can be reduced.

In Embodiment 3, the light absorber 306 does not necessarily have to cover an entire curved surface of the window portion 305, and it is sufficient if at least a part of the curved surface is covered, and thereby the ultrasonic waves can be transmitted from the portion.

Embodiment 4

The technique described in Embodiments 1 to 3 is a technique of specifying the position of the ultrasonic transmission source provided in the treatment instrument. On the other hand, providing of the transparent window portion has an effect in addition to the above-described uniform generation of ultrasonic waves. Specifically, by setting a structure of the transparent window portion to a shape whose angle can be defined, it is possible to measure the angle in addition to the position of the treatment instrument. Angle information is useful for uses such as determining a traveling direction of the treatment instrument. Therefore, in Embodiment 4 of the invention, a method of detecting an angle of a small-diameter treatment instrument by setting the shape of the transparent window portion to the shape whose angle can be defined will be described.

The shape whose angle can be defined is exactly a shape in which when a certain shape is rotated by a specific angle, the shape is not the same as before rotation. When the shape is spherical, the angle cannot be defined because the shape does not change by a rotation operation. In a case of a rectangular parallelepiped that has three sides with different lengths, the shape is the same when rotated by 180°, but is not the same when rotated by other angles. In order to realize an angle measurement function, it is necessary that the shape is not the same for the rotation operation of at least one angle, but the higher the symmetry, the angle at which the rotation cannot be recognized increases, for example, a rotation of 180° in a rectangular parallelepiped, so that a shape with low symmetry is desirable. As an example, in a case of a cube, since the shape is the same as before rotation when rotated by 90° and 180°, the rectangular parallelepiped (having three sides with different lengths) whose shape is the same as before rotation only when rotated by 180° is more desirable than the cube. Since this shape needs to be imaged by an ultrasonic imaging device, a size of this shape needs to be higher than a resolution of the ultrasonic imaging device.

Figure 12:
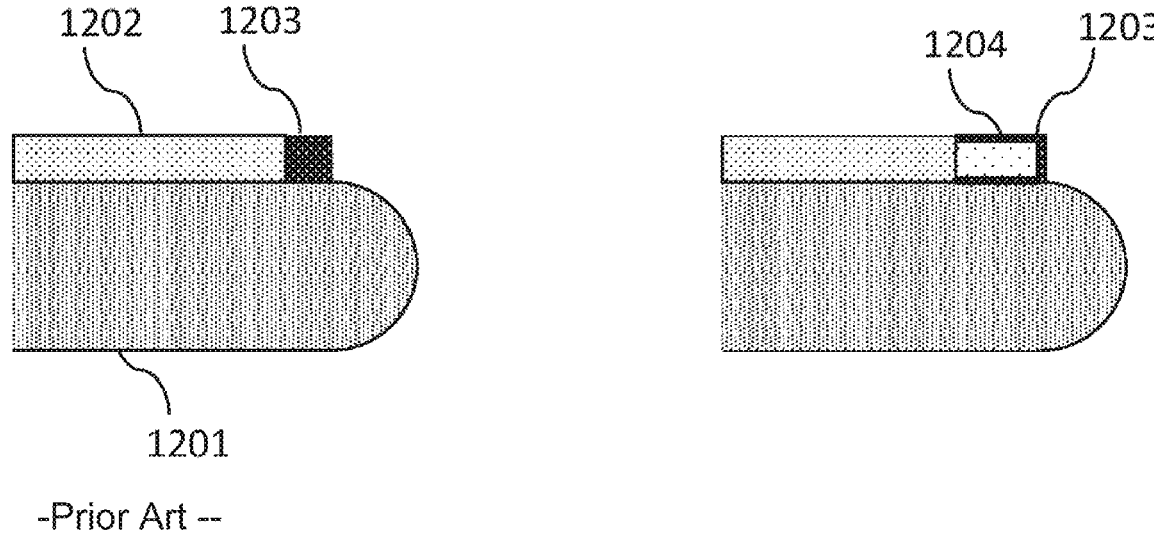
FIG. 12 shows an example of a shape of an ultrasonic transmission source according to Embodiment 4.

FIG. 12 shows an example of a shape of an ultrasonic transmission source according to Embodiment 4. A left side of FIG. 12 shows, taking a shape of the ultrasonic transmission source using the photo-acoustic effect described in PTL 1 or the like as an example, an example in which the ultrasonic transmission source is attached to a wire. A right side of FIG. 12 shows a structure of the ultrasonic transmission source according to Embodiment 4.

An optical fiber 1202 is disposed along a wire portion 1201, and a light absorber 1203 is provided at a tip end of the optical fiber 1202. An ultrasonic wave is generated from the light absorber 1203 by introducing pulse laser light into the optical fiber 1202. As in Embodiment 1, the ultrasonic wave is received by the ultrasonic probe, an image is constituted based on a received signal waveform, and a position of the ultrasonic transmission source is specified.

The ultrasonic transmission source according to Embodiment 4 differs from an example in the related art shown in a left side of FIG. 12 in that a transparent window portion 1204 is provided at the tip end of the optical fiber 1202. The light absorber 1203 is provided on a surface of the transparent window portion 1204. A feature of Embodiment 4 is that the transparent window portion 1204 and the light absorber 1203 have a structure whose angle can be defined. As an example, as described above, a shape of the window portion 1204 may be a rectangular parallelepiped with three different sides. The window portion 1204 may be made of a material including a light scatterer in order to make a generation intensity of the ultrasonic wave uniform.

Figure 13:
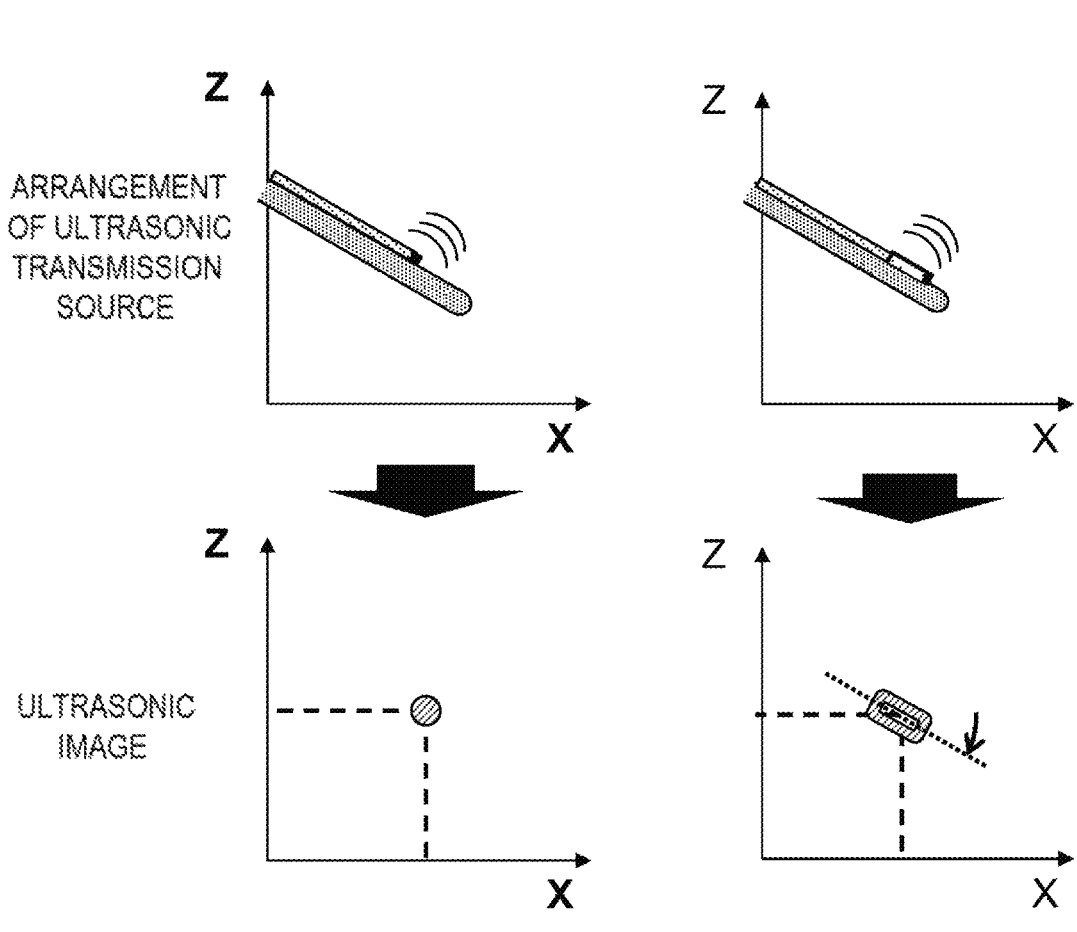
FIG. 13 is a diagram showing an angle detection method according to Embodiment 4.

FIG. 13 is a diagram showing an angle detection method according to Embodiment 4. A left side of FIG. 13 shows a method in the related art, and a right side of FIG. 13 shows a method in the present technique. In the related art, as an example, a signal from the ultrasonic transmission source is imaged, and a point having the highest signal intensity in the image is detected as the position of the ultrasonic transmission source, as shown in the left side of FIG. 13. In Embodiment 4, the shape of the ultrasonic transmission source is non-rotationally symmetric. As an example, in a case where a cross-section of the shape of the ultrasonic transmission source is rectangular as shown in the right side of FIG. 13, when a generated ultrasonic signal is imaged, the image of the ultrasonic transmission source is also rectangular. For example, a center position can be measured by obtaining a center of gravity of an ultrasonic intensity of the rectangle. In addition, by measuring an inclination of a long side of the rectangle, an inclination of the treatment instrument can be measured.

In a known example such as PTL 1, a dye for transmitting an ultrasonic wave is provided at a tip end portion of an optical fiber. In general, a thickness of the optical fiber is about several hundred µm, even when the ultrasonic wave transmitted from the tip end is imaged, the ultrasonic wave can be seen as only one point on the image, and it is difficult to define a direction. As in the structure according to Embodiment 4, it is essentially important to provide an ultrasonic transmission source whose angle can be defined and whose size can be determined on an ultrasonic image.

Figure 14:
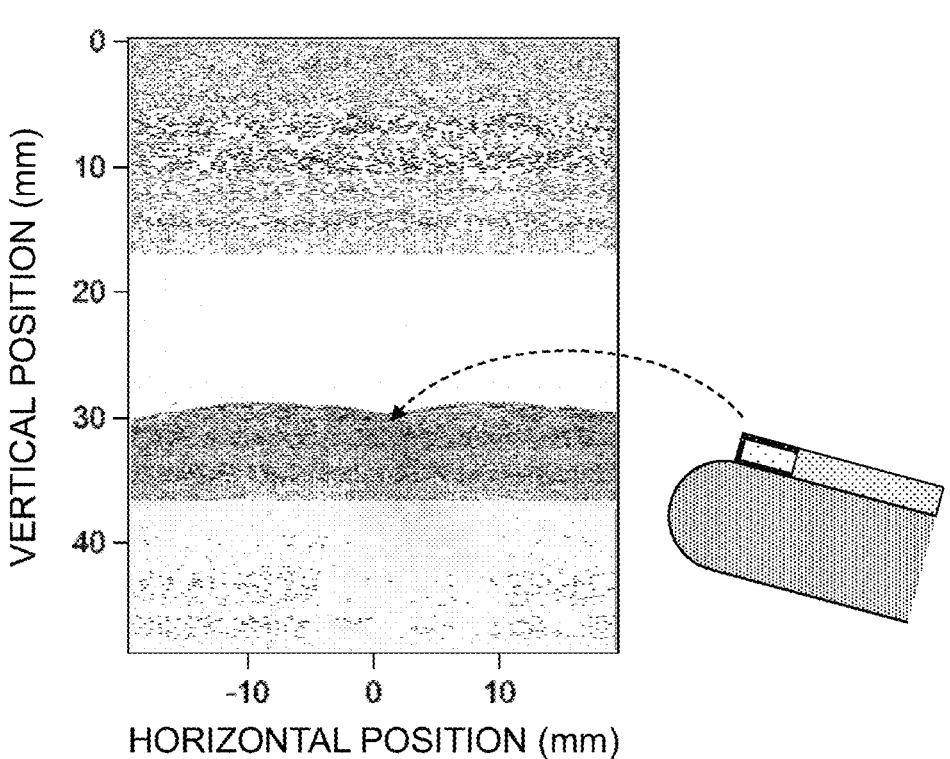
FIG. 14 shows a result of verifying an effect of Embodiment 4 by an experiment.

FIG. 14 shows a result of verifying an effect of Embodiment 4 by an experiment. An ultrasonic transmission source used in FIG. 14 has the structure shown in the right side of FIG. 12. A transparent silicon rubber shaped into a rectangular parallelepiped is attached to a tip end of an optical fiber, and a light absorber is applied to a surface thereof. FIG. 14 shows a state in which the ultrasonic transmission source is mounted on a metal rod and an image is reconstituted based on a generated ultrasonic signal. In the ultrasonic transmission source used in this experiment, the light absorbers are applied to all five surfaces of the silicon rubber rectangular parallelepiped except for a surface in contact with the optical fiber, so that on an ultrasonic tomographic image, three surfaces of an upper surface, a lower surface, and a tip end surface are U-shaped.

In a case of detecting the position of the ultrasonic transmission source based on FIG. 14, as an example, a center position of an image of a surface of the tip end portion (the portion corresponding to a U-shaped vertical rod) may be recognized as the tip end of the ultrasonic transmission source. In a case of measuring an inclination, as an example, an inclination of a line corresponding to the upper surface may be detected.

Figure 15:
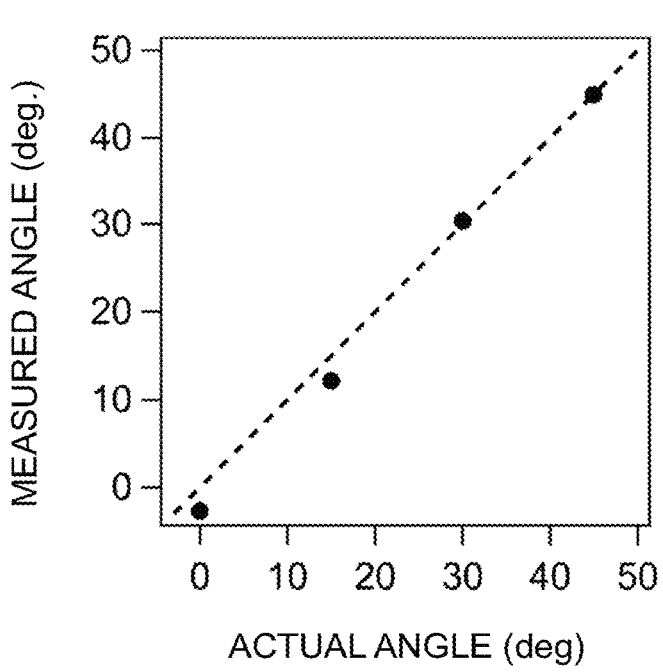
FIG. 15 is a graph in which a measurement result of an inclination angle of an upper surface is plotted.

FIG. 15 is a graph in which a measurement result of an inclination angle of the upper surface is plotted. In FIG. 15, an angle of the ultrasonic transmission source is changed in a range of 0 to 45 degrees, an actual angle is shown on a horizontal axis, and a result of measuring the angle is shown on a vertical axis. With respect to an ideal estimated straight line drawn by a dotted line, black points indicating actual measurement results have an error of ±5 degrees or less, and it can be seen that the angle measurement is performed correctly.

Figure 16:
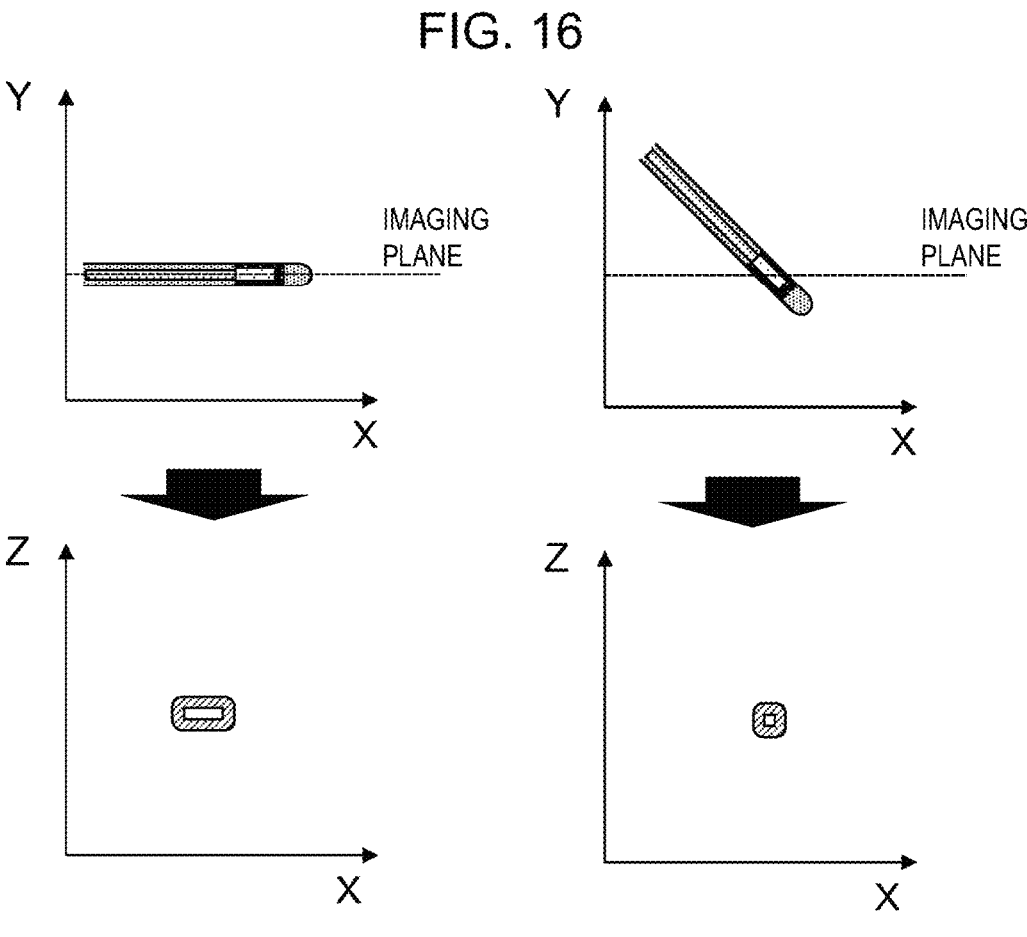
FIG. 16 is a diagram showing an angle detection method in a direction outside an ultrasonic imaging plane according to Embodiment 4.

The above method detects a rotation angle in an ultrasonic imaging plane, and a rotation angle in a plane perpendicular to the ultrasonic imaging plane can also be estimated. FIG. 16 shows a method of detecting a rotation angle in a plane perpendicular to the ultrasonic imaging plane. A left side of FIG. 16 shows a case where an ultrasonic imaging cross-section and a direction of the ultrasonic transmission source are aligned. In this case, a cross-section of the ultrasonic transmission source in a long axis direction is observed. A right side of FIG. 16 shows a situation when the ultrasonic transmission source is inclined with respect to the ultrasonic imaging plane. In this case, when a rotation angle is 8, a length of the ultrasonic transmission source in an X-axis direction is cos θ times an original length. Therefore, if a true length of the ultrasonic transmission source is stored inside a system, a ratio of a length of the ultrasonic transmission source actually measured from the ultrasonic image to the true length is obtained, and the rotation angle in a plane perpendicular to the ultrasonic imaging plane can be measured by obtaining an inverse cosine of the ratio. In this direction, a direction of the rotation cannot be measured. It is because the same ultrasonic image is obtained when, for example, the rotation is +45° and the rotation is −45°. In order to detect the direction of the rotation, additional information and a sensor are required.

Figure 17:
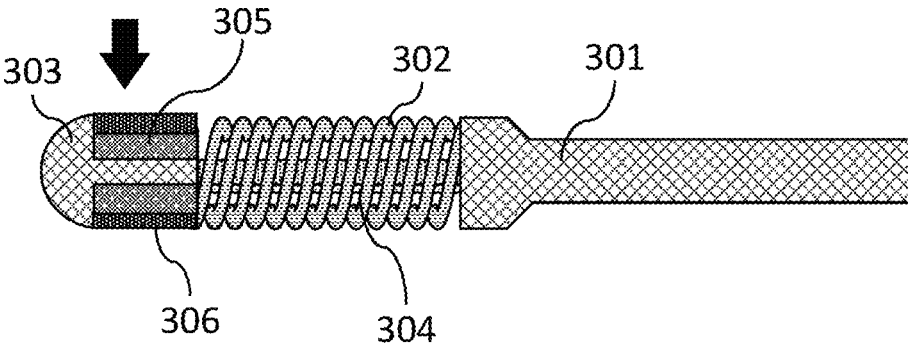
FIG. 17 shows an example in which the ultrasonic transmission source according to Embodiment 4 is incorporated into a guide wire for vascular treatment.

FIG. 17 shows an example in which the ultrasonic transmission source according to Embodiment 4 is incorporated into a guide wire for vascular treatment. The effect of Embodiment 4 is described by taking the case where the cross-sectional shape is rectangular as an example, but the shape of the ultrasonic transmission source may be any other shape as long as the direction for the angle detection can be defined. In FIG. 17, as in Embodiment 1, the coil portion 302 and the tip end portion 303 are provided at the tip end of the wire portion 301, and the optical fiber 304 is attached along the structure. The transparent window portion 305 is provided behind the tip end portion 303, and the light absorber 306 is provided on the surface thereof. When the ultrasonic image is reconstituted, the light absorber 306 is imaged. The light absorber 306 has a cylindrical shape, and appears as two lines on a tomographic image. Therefore, an inclination of the tip end portion of the guide wire can be detected by measuring an angle of one or both of these two lines.

Figure 18:
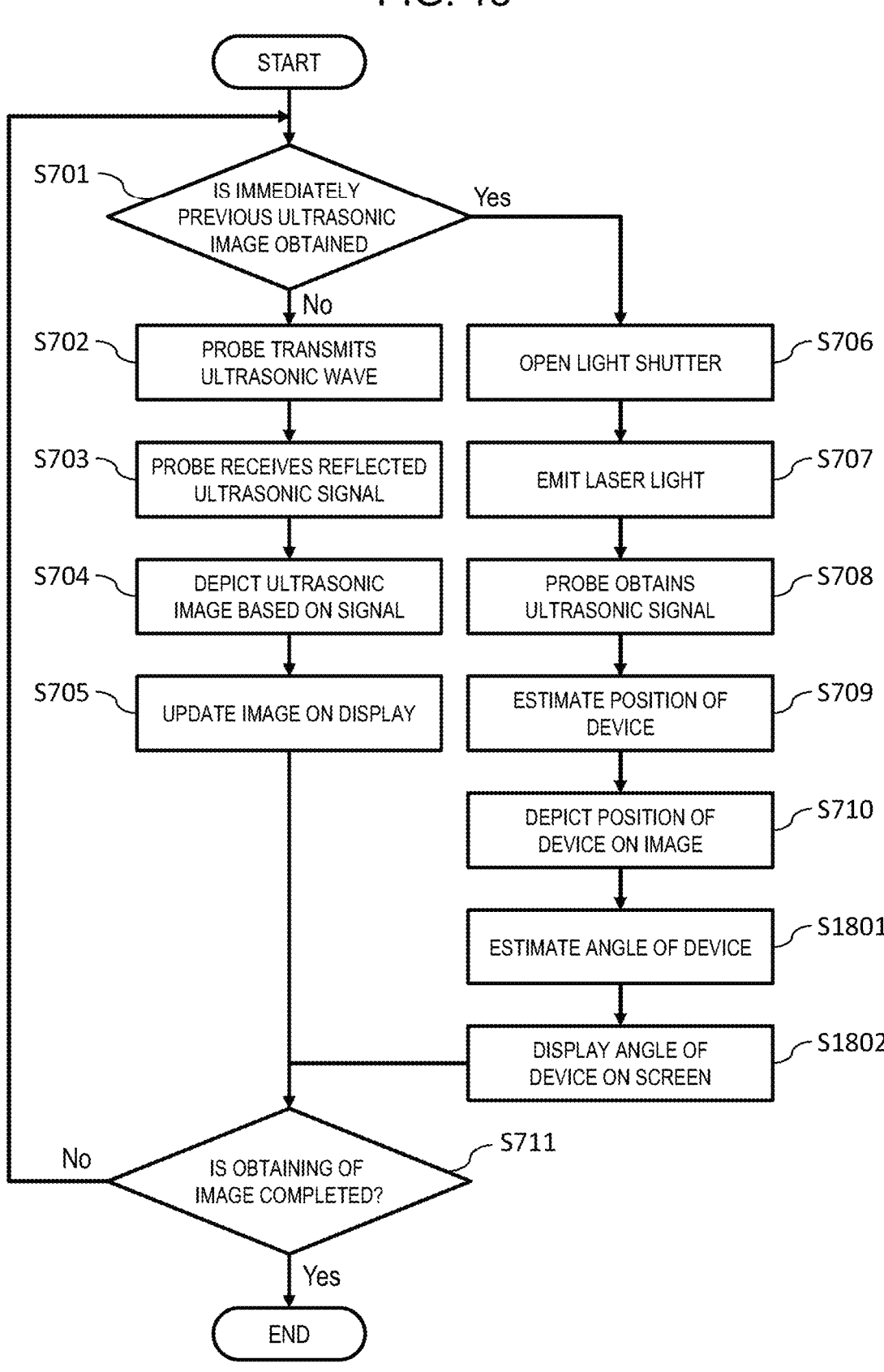
FIG. 18 is a flowchart showing an operation sequence of the position detection system 200 according to Embodiment 4.

FIG. 18 is a flowchart showing an operation sequence of the position detection system 200 according to Embodiment 4. A configuration of the position detection system 200 is the same as that of Embodiment 1. Steps S701 to S711 are the same as those in Embodiment 1. In Embodiment 4, after depicting the position of the treatment instrument, the system estimates the angle based on the image of the non-rotationally symmetric ultrasonic transmission source (S1801). Thereafter, the angle is displayed on a screen such that a user can visually recognize the angle (S1802).

Embodiment 4: Overview

The ultrasonic transmission instrument according to Embodiment 4 is configured such that the window portion 305 through which light is transmitted is disposed in the small-diameter instrument such as a catheter, and the light absorber 306 for generating the photo-acoustic signal is disposed on the outer peripheral portion of the window portion 305. In order to make it possible to detection the position and angle of the ultrasonic transmission source, the window portion 305 and the light absorber 306 have a shape (for example, a rectangular parallelepiped or a column having a rectangular cross-section with a long side) whose angle can be defined. Accordingly, the position and the angle of the small-diameter treatment instrument provided with the ultrasonic transmission source can be measured.

Modification of Invention

The invention is not limited to the embodiments described above, and includes various modifications. For example, the above-described embodiments have been described in detail for easy understanding of the invention, and are not necessarily limited to those having all the configurations described above. Further, a part of the configuration of a certain embodiment can be replaced with the configuration of another embodiment, and the configuration of a certain embodiment can be added to the configuration of another embodiment. Further, a part of the configuration of each embodiment can be combined to, omitted from, or replaced with another configuration.

In the above embodiments, the window portion 305 does not necessarily need to transmit 100% of light. That is, a function as the window portion 305 can be exhibited as long as at least a part of light emitted from the optical fiber 304 can reach the light absorber 306 and generate an ultrasonic wave by the photo-acoustic effect.

In the above embodiments, since the tip end portion 303 is a member for increasing strength of the tip end portion of the guide wire 204, the tip end portion 303 is typically formed of a metal member. In this case, the tip end portion 303 is a member that completely blocks light. However, the tip end portion 303 does not necessarily need to completely block the light, and may transmit a part of the light as long as the light absorber 306 is not hindered from generating an ultrasonic wave by the photo-acoustic effect. Further, the tip end portion 303 does not necessarily need to cover the entire tip end of the guide wire 204, and may cover the tip end to such an extent that the strength can be increased.

In the above embodiments, the light absorber 306 is disposed on the outer periphery of the window portion 305. Here, the outer periphery does not necessarily need to be the outermost periphery of the guide wire 204 (or the small-diameter instrument 1001). For example, in FIG. 11, another member (such as a coating coat) through which an ultrasonic wave can be transmitted may be disposed further outside the light absorber 306. In other words, other members may be present around the window portion 305 and the light absorber 306 as long as the ultrasonic wave can be transmitted by configuring any member that transmits light as the window portion 305, and disposing the light absorber 306 on the outer peripheral portion of the window portion 305, which is the same in each embodiment.

The structures described in the above embodiments are applicable to instruments that are inserted into the body under the ultrasonic imaging guide, and are also applicable to other small-diameter instruments whose outer peripheral portion is configured with the light absorber 306.

What is claimed is:

1. An ultrasonic transmission instrument configured to transmit an ultrasonic wave, the ultrasonic transmission instrument comprising:
   an optical waveguide that is disposed inside the ultrasonic transmission instrument;
   a light transmission member that surrounds a wire member, wherein the light transmission member is configured to transmit at least a part of light emitted from the optical waveguide;
   an outer peripheral member that covers at least a part of an outer periphery of the light transmission member, wherein the outer peripheral member is made of a light absorbing material that is configured to generate the ultrasonic wave by absorbing the light and the light absorbing material has a shape that is not symmetric with respect to a rotation operation of at least one angle.

2. The ultrasonic transmission instrument according to claim 1,
   wherein the light transmission member is attached so as to cover an emission end of the optical waveguide from which the light is emitted.

3. The ultrasonic transmission instrument according to claim 2, wherein
   the light transmission member has a cylindrical shape,
   a bottom surface of the light transmission member is disposed at a position covering the emission end, and
   the outer peripheral member covers at least a part of a side surface of the light transmission member.

4. The ultrasonic transmission instrument according to claim 2, further comprising:
   an opaque member configured to block at least a part of the light, wherein
   the light transmission member is disposed between the emission end and the opaque member, and
   the opaque member is disposed so as to cover at least a part of the light transmission member that is not covered by the outer peripheral member.

5. The ultrasonic transmission instrument according to claim 4, wherein
   the opaque member is attached to an end of the wire member.

6. The ultrasonic transmission instrument according to claim 2, wherein
   one end of the light transmission member has a curved surface,
   the other end of the light transmission member is disposed at a position for receiving the light emitted from the emission end, and
   the outer peripheral member covers at least a part of the curved surface.

7. The ultrasonic transmission instrument according to claim 6, further comprising:
   a light scattering member that scatters the light emitted from the optical waveguide inside the light transmission member.

8. The ultrasonic transmission instrument according to claim 1, further comprising:

a light scattering member configured to scatter the light emitted from the optical waveguide inside the light transmission member.

9. The ultrasonic transmission instrument according to claim 8,
   wherein the light scattering member is disposed at an emission end of the optical waveguide from which the light is emitted.

10. The ultrasonic transmission instrument according to claim 1, further comprising:
   a hollow portion, wherein
   the optical waveguide is disposed on an outer periphery of the hollow portion, and
   the light transmission member is disposed on the outer periphery of the hollow portion.

11. The ultrasonic transmission instrument according to claim 1,
   wherein a cross-sectional shape of the light absorbing material is rectangular.

12. An ultrasonic imaging device configured to generate an image of a subject using an ultrasonic wave, the ultrasonic imaging device comprising:
   an ultrasonic transmission instrument configured to transmit the ultrasonic wave, wherein ultrasonic transmission instrument includes:
   an optical waveguide that is disposed inside the ultrasonic transmission instrument;
   a light transmission member configured to transmit at least a part of light emitted from the optical waveguide; and
   an outer peripheral member that covers at least a part of an outer periphery of the light transmission member;
   an ultrasonic probe configured to receive a reflected ultrasonic wave that is generated by the ultrasonic wave reflecting from the subject, wherein the ultrasonic probe includes a plurality of elements;
   an image generation unit configured to generate an ultrasonic image of the subject using the reflected ultrasonic wave received by the ultrasonic probe;
   a position estimation unit configured to estimate a position of the ultrasonic transmission instrument using a difference between time points when respective elements among the plurality of elements receive the reflected ultrasonic wave; and
   an angle estimation unit configured to estimate an inclination of the ultrasonic transmission instrument based on a shape of the image of the outer peripheral member in the ultrasonic image generated by the image generation unit,
   wherein the outer peripheral member is made of a light absorbing material that generates the ultrasonic wave by absorbing the light and the outer peripheral member has a shape that is not symmetric with respect to a rotation operation of at least one angle.

13. The ultrasonic imaging device according to claim 12,
   wherein the angle estimation unit configured to measure an inclination of an image of the ultrasonic transmission instrument based on the ultrasonic image generated by the image generation unit, and estimates an angle in an ultrasonic image plane.

14. The ultrasonic imaging device according to claim 13,
   wherein the angle estimation unit is configured to measure the inclination measures a length of the image of the ultrasonic transmission instrument based on the ultrasonic image of the subject generated by the image, and estimates an angle in a plane perpendicular to the ultrasonic image by obtaining a ratio of the length to a true length of the ultrasonic transmission instrument measured in advance.

* * * * *